(12) United States Patent
Luxon et al.

(10) Patent No.: US 9,050,153 B2
(45) Date of Patent: Jun. 9, 2015

(54) UNIVERSALLY DEPLOYABLE AND EXPANDABLE BONE SCREW ANCHOR

(75) Inventors: Evan Scott Luxon, Omaha, NE (US); Jason Joseph Hsu, San Jose, CA (US); Christopher Bligh Komanski, Gainesville, FL (US); Nicolas Alejandro Martinez, Palmetto Bay, FL (US); A. Jay Khanna, Potomac, MD (US)

(73) Assignee: The Johns Hopkins University, Baltimore, MD (US)

( * ) Notice: Subject to any disclaimer, the term of this patent is extended or adjusted under 35 U.S.C. 154(b) by 346 days.

(21) Appl. No.: 13/505,602

(22) PCT Filed: Nov. 4, 2010

(86) PCT No.: PCT/US2010/055476
§ 371 (c)(1),
(2), (4) Date: Jul. 12, 2012

(87) PCT Pub. No.: WO2011/056990
PCT Pub. Date: May 12, 2011

(65) Prior Publication Data
US 2012/0271363 A1 Oct. 25, 2012

Related U.S. Application Data

(60) Provisional application No. 61/258,362, filed on Nov. 5, 2009.

(51) Int. Cl.
*A61B 17/86* (2006.01)

(52) U.S. Cl.
CPC ......... *A61B 17/8625* (2013.01); *A61B 17/8685* (2013.01); *A61B 17/869* (2013.01)

(58) Field of Classification Search
CPC ..... A61B 17/702; A61B 17/86; A61B 17/864
USPC ............ 606/300, 301, 309, 310, 313; 411/55, 411/57.1, 80.1, 80.5
See application file for complete search history.

(56) References Cited

U.S. PATENT DOCUMENTS

| | | | |
|---|---|---|---|
| 4,610,587 A * | 9/1986 | Wollar et al. | 411/80.1 |
| 5,522,843 A | 6/1996 | Zang | |
| 6,613,053 B1 * | 9/2003 | Collins et al. | 606/293 |
| 6,733,502 B2 | 5/2004 | Altarac et al. | |
| 7,655,046 B2 * | 2/2010 | Dryer et al. | 623/17.15 |
| 8,038,375 B2 * | 10/2011 | Kohan et al. | 411/80.5 |
| 2002/0147454 A1 * | 10/2002 | Neto | 606/73 |
| 2006/0015105 A1 | 1/2006 | Warren et al. | |
| 2006/0235403 A1 | 10/2006 | Blain | |
| 2009/0171396 A1 | 7/2009 | Baynham et al. | |

* cited by examiner

*Primary Examiner* — Anu Ramana
(74) *Attorney, Agent, or Firm* — DLA Piper LLP (US)

(57) ABSTRACT

A self-expanding bone screw anchor assembly adapted to allow the screw body to engage the bone and the anchor to attach thereto. The anchor assembly is adapted to be universally deployed with a variety of installation tools.

19 Claims, 6 Drawing Sheets

UNIVERSALLY DEPLOYABLE AND EXPANDABLE BONE SCREW ANCHOR

CROSS REFERENCE TO RELATED APPLICATIONS

This application is a 35 USC §371 National Stage application of International Application No. PCT/US2010/055476 filed Nov. 4, 2010, now pending; which claims the benefit under 35 USC §119(e) to U.S. Application Ser. No. 61/258,362 filed Nov. 5, 2009. The disclosure of each of the prior applications is considered part of and is incorporated by reference in the disclosure of this application.

FIELD OF THE INVENTION

The invention relates to devices for securing an implantable medical device into bone. More specifically, the invention relates to devices for use in spinal surgery to deploy spinal stabilization or fixation devices including bone screws.

BACKGROUND OF THE INVENTION

Bone in human and other mammal bodies is generally classified into two types, cortical bone, also known as compact bone and trabecular bone, also known as cancellous or spongy bone. Cortical bone is much denser with a porosity ranging between 5% and 10%. Cortical bone is found primary is found in the shaft of long bones and forms the outer shell around cancellous bone at the end of joints and the vertebrae.

In the vertebrae, each bone is generally heart shaped, with spinous, inferior and superior processes joined to the vertebral body via opposing pedicles. To stabilize or fix the spine, implantable medical devices can be employed between adjacent vertebrae, and attached via screws through the pedicles (i.e., via "pedicle screws") and other osseous structures such as the lamina and facet joints.

The outer bony shell of the pedicles is formed of dense cortical bone, which surrounds spongier cancellous bone. In degenerative conditions such as osteoporosis or following injury, the cancellous bone can weaken and degrade. Cancellous bone can also be displaced through installation of a pedicle screw.

Screws of all sizes can loosen or shift position if placed in osteoporotic or otherwise weak cancellous bone. Pedicle screws are available which seek to avoid loosening or shifting in place through installation with an expandable anchor. In most such designs, the anchor includes deflectable wings at the distal tip which will push outwardly against the bone as the pedicle screw is inserted through the anchor in a fashion similar to screw anchors used in building walls. However, the cylindrical design of such anchors provides relatively minimal interaction between the body of the screw and bone. They also tend to rely primarily on friction to secure the anchor, which can close and lose essential contact as the cancellous bone further degrades.

Another drawback of many existing pedicle screw implants is the lack of adaptability to use with different surgical devices. In particular, pedicle screws of differing diameters, whether monoaxial or polyaxial in design, generally include a screw head for engaging an installation device, or a headless design. In both instances, the installation device must generally be matched in size and shape to the pedicle screw head or other proximal screw surface, requiring a selection of tools to be available for use with different patients.

SUMMARY OF THE INVENTION

In a first aspect, the invention provides a self-expanding bone screw anchor assembly adapted to allow the screw body to engage the bone and the anchor to attach thereto. The anchor may be fully or partially inserted, followed by insertion of the bone screw.

The anchor has a body with a partially open cylindrical design with a shaft extending between proximal and distal ends. At least two opposing vertical slots are disposed along the shaft body, through which helical turns of a screw body may protrude to engage surrounding bone. The material of the anchor body adjacent the slots form vertical walls which, at their distalmost end, are deflectable to form anchoring wings to engage the surrounding bone.

To strengthen the deflectable wings while limiting their ability to disengage from bone, a deflectable collar is provided within the interior diameter of the shaft proximal to the wings. Insertion of the screw through the collar causes it to expand and stiffen, reinforcing the shaft walls above the distal wings.

In another aspect, the distal wings are hinged to provide for controlled outward expansion on insertion of a bone screw.

In an optional aspect, one or more pairs of opposing outwardly deflectable flanges are provided along the shaft walls. To minimize the outer diameter of the anchor body during insertion into bone, the flanges are retracted within the diameter of the shaft until insertion of the screw through the lumen of the shaft. As it passes through the lumen, the screw body pushes each flange outwardly to engage the surrounding cancellous bone. Engagement of the flanges by the bone further secures the anchor and screw against dislodgment, even with some cancellous bone degradation.

In another aspect of the invention, the flanges are hinged to the shaft walls for controlled outward expansion on insertion of a bone screw.

In yet another aspect, the anchor includes a universally adaptable screw head or nut to facilitate its insertion into bone. The screw head is made of a deformable material which can stretch in diameter and shape to accommodate different sizes and shapes of installation tools and bone screws.

In another aspect, the screw head is a nut that can be removed following implantation of the anchor assembly, including a screw.

Additional systems, methods, features, and advantages of the invention will be apparent to one with skill in the art on consideration of this disclosure, including references cited therein, each of which is incorporated into the disclosure by this reference. It is intended that all such additional systems, methods, features, and advantages be included within this description, be within the scope of the invention, which is defined solely by the appended claims.

BRIEF DESCRIPTION OF THE DRAWINGS

The following drawings may contain hidden features or elements shown in dotted lines and may include phantom views of various components or elements shown in dashed-dotted lines. In all drawings, representative dimensional characteristics are indicated.

In FIG. 1A, line A-A represents the junction between the anchor body proper and the distal wings.

DETAILED DESCRIPTION OF THE INVENTION

Figure 1A:
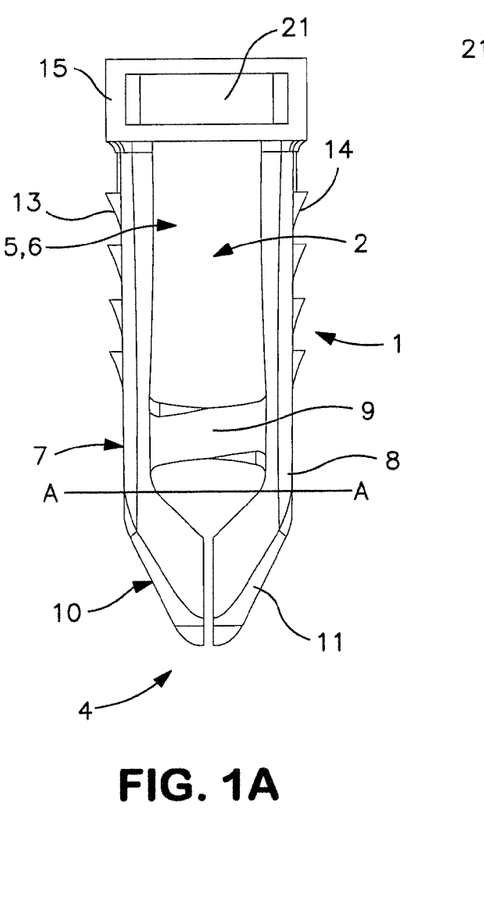
FIGS. 1A and 1B provide front (A) and side (B) views of the anchor assembly.
Figure 1B:
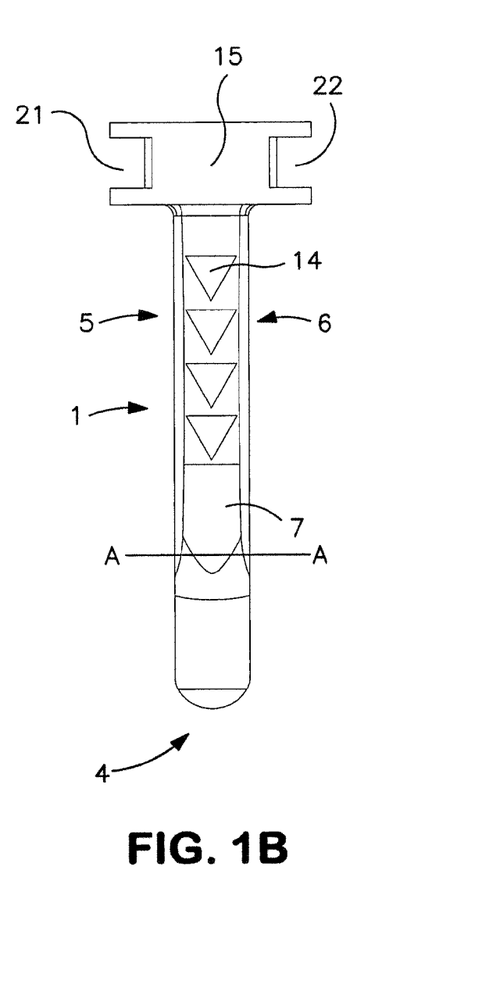

Referring to FIGS. 1A and 1B, the anchor assembly comprises elongate body 1, defining lumen 2 therethrough. The lumen provides a bore through the device having an inner diameter that allows for the insertion of a screw body such as bone (pedicle) screws or setting rods and seating therein.

Elongate body 1 has a partially open cylindrical design with a shaft extending between proximal and distal ends 3 and 4. At least two opposing vertical slots 5 and 6 are disposed along the shaft body, through which helical turns of a screw body may protrude to engage surrounding bone, thereby stabilizing the screw within the bone. Slots 5, 6 extend vertically to about ⅔ to ¾ the length of the elongate body and circumferentially to up to 75% of the body diameter. The remaining material forms opposing walls of the shaft body 7 and 8, which walls are curved (e.g., in substantially a "c" shape).

At the distalmost end (below line A-A of FIG. 1A), walls 7, 8 are tapered inwardly as well as outwardly deflectable on insertion of a bone screw; i.e., the ends can extend away from body 1 to form wings 10 and 11. As discussed further hereinbelow, wings 10, 11 may be symmetrical or asymmetrical, as shown in expanded state in FIGS. 2A and 2B. In either configuration, the wings are outwardly deflectable from the anchor body to form an angle therefrom of 10 to 60°, most preferably between 25 and 45°.

Figure 3:
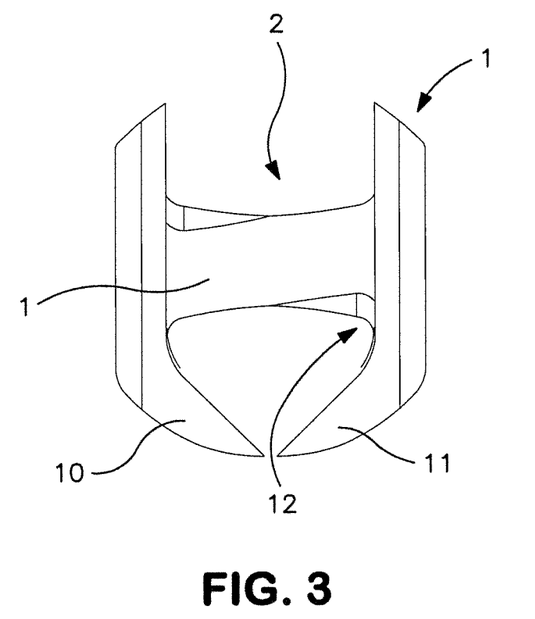
FIG. 3 provides a side view of the unexpanded collar.
Figure 4:
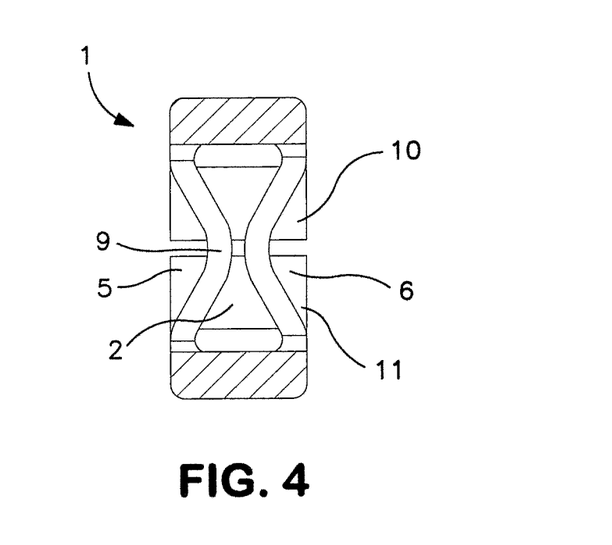
FIG. 4 provides a top view of the unexpanded collar.
Figure 5A:
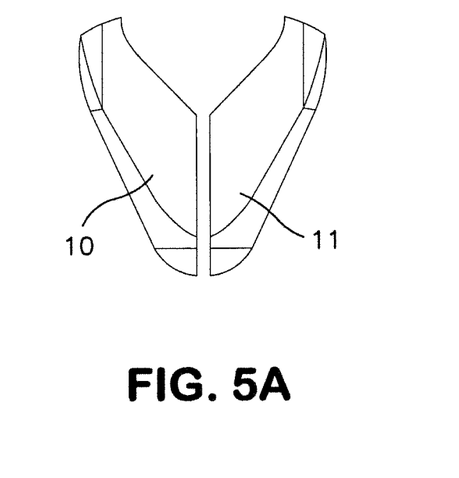
FIGS. 5A and 5B provide side and front views of a wing in a non-deflected state.
Figure 5B:
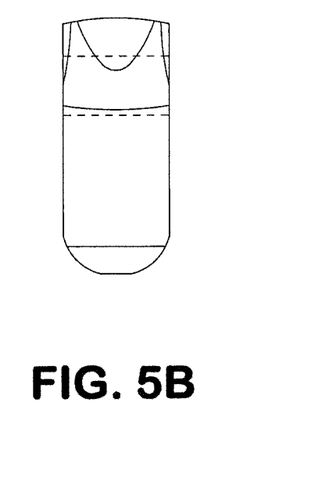

As detailed in FIGS. 3 and 4, to strengthen the deflectable wings while holding preventing distortion of the shaft walls, to maximize the deflecting force exerted on the wings, a deflectable collar 9 is provided within the diameter of elongate body 1 proximal to wings 10, 11. Prior to insertion of a screw through lumen 2, collar 9 rests in an unexpanded inverted shape that is preferably concave in its center (forming a loose FIG. 8) at the vertical openings of the shaft to minimize the hole diameter into which the anchor must be seated in the bone. Insertion of the screw through the collar exerts compressive force against the internal surface of the collar, causing it to expand and stiffen, forming a shape (preferably circular) which protrudes from vertical slots 5, 6, thereby engaging surround bone and reinforcing the shaft walls above wings 10 and 11. Most preferably, the sides of collar 9 are slightly offset from horizontal; i.e., by between 5° and 10° (for example, by 8° as shown in FIG. 3). Alternatively, when unexpanded, the collar may assume any shape (e.g., straight parallel walls) whose walls do not protrude through vertical slots 5, 6 prior to expansion, and through which a bone screw may be inserted.

Wings 10, 11 may be deflectable in response to a compressive force exerted by insertion of the screw through lumen 2, wherein the deflection is provided by virtue of flexibility in the material used in body 1 as described below. Preferably, however, wings 10, 11 are each provided with a hinge 12 for controlled outward expansion on insertion of a bone screw through the length of lumen 2.

Figure 2A:
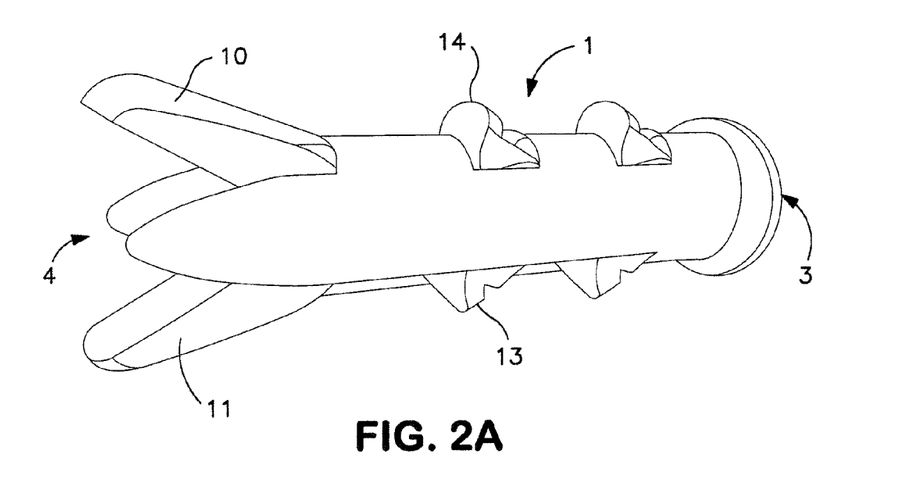
FIGS. 2A and 2B provide side view of the anchor assembly with, respectively, symmetrical and asymmetrical unexpanded wings.
Figure 2B:
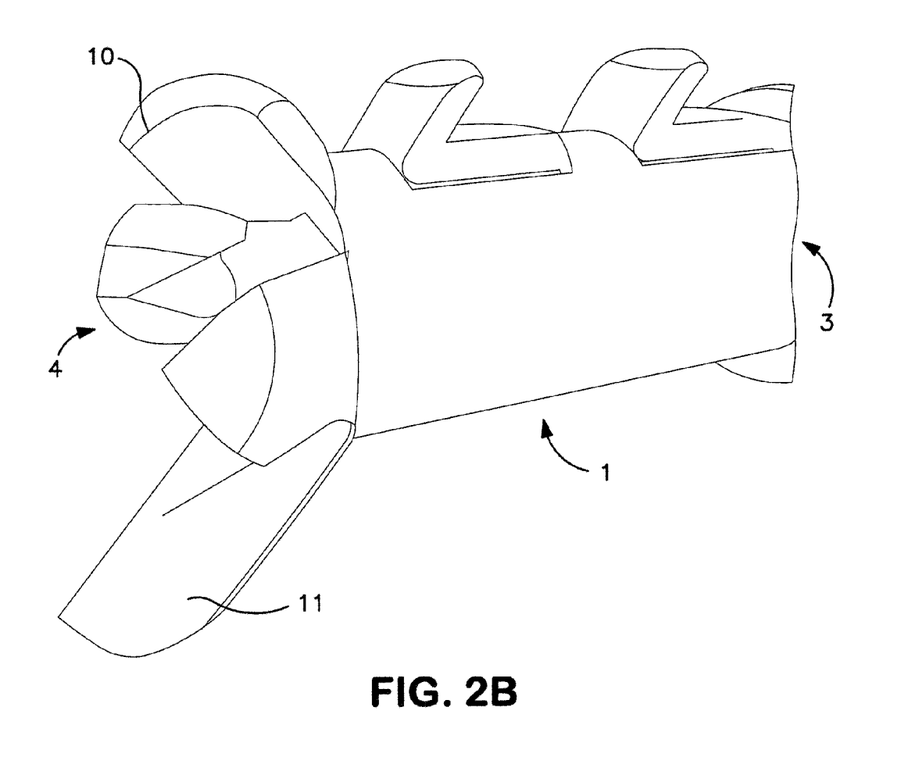

As shown in FIG. 2A, wings 10, 11 are symmetrical in placement and length on body 1. Alternatively, wings 10, 11 may be asymmetrically disposed on body 1 as illustrated in FIG. 2B. The asymmetrical configuration allows wings 10, 11 to be displaced at specific and independent distances and angles in the superior, inferior, medial, and lateral directions.

To allow for deflectability of wings 10 and 11, elongate body 1 is preferably a biocompatible polymer with a degree of flexibility. Those of ordinary skill in the art will be familiar with materials available for use in bone screw anchors which include, without limitation, a medical grade polymer or titanium. Numerous medical grade polymers exist such as nylon, polyetheretherketone (PEEK), high density polyethylene, ultra-high molecular weight or high modulus polyethylene, polyethylene glycol, polyvinyl chloride (PVC), polymethyl methacrylate (PMMA), polyvinyl alcohol (PVA), etc. Additional materials of use in the invention include titanium, nitinol and stainless steel.

If hinged, however, deflection of wings 10, 11 may occur by rotation of hinge 12 at each wing. Hinge 12 attach wings 10, 11 to walls 7, 8. Hinge 12 may secured to walls 7, 8 by any means suitable for deployment in an implantable medical device, including a biocompatible metal or polymer pin, groove and socket hinges, and similar structures.

Referring to FIGS. 3 and 4, collar 9 may be formed of the same material or a more elastic one, having sufficient rigidity to retain the unexpanded concavity described herein while being expandable on insertion of a screw body therethrough. Such materials include, without limitation, those described above with respect to suitable materials for body 1, including wings 10, 11.

Figure 6:
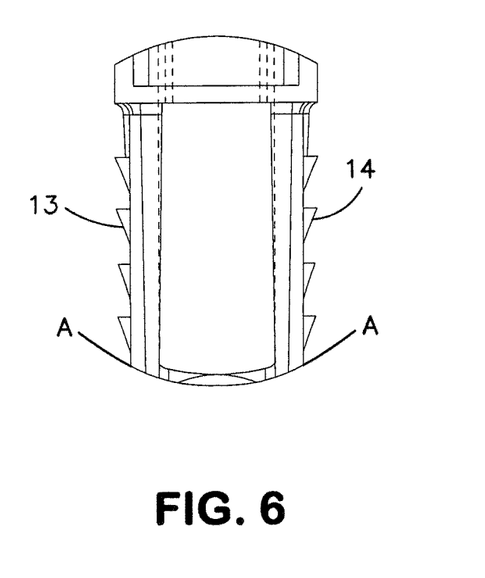
FIG. 6 provides a front view of the anchor body deflectable flanges.
Figure 7:
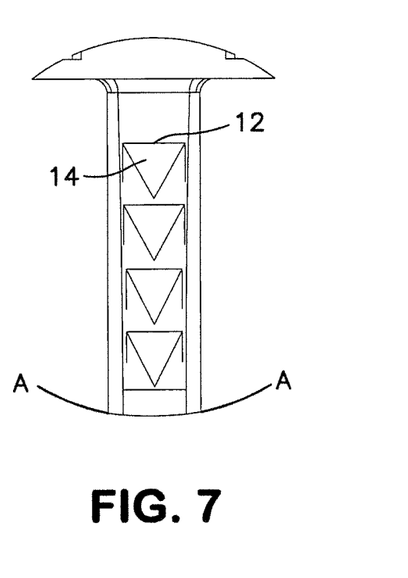
FIG. 7 provides a side view of the anchor body deflectable flanges.

In an alternative embodiment which provides additional stability to the anchor (especially for use with significantly degraded bone), body 1 is further stabilized within the bone on insertion by engagement of flanges along body 1 with surrounding bone. To that end, one or more pairs of opposing outwardly deflectable flanges 13 and 14 are provided along walls 7, 8 (see FIGS. 6 and 7), situated on body 1 above line A-A (see FIG. 1A). To minimize the outer diameter of elongate body 1 during insertion into bone, one or more pairs of flanges 13, 14 are retracted within lumen 2 so as not to extend beyond the outer diameter of body 1 until insertion of a screw body through lumen 2. As it passes through lumen 2, the screw body pushes each flange pair 13, 14 deflect outwardly to engage the surrounding bone.

Each flange 13, 14 is attached to walls 7, 8 by a hinge 12 for controlled outward expansion on insertion of a screw body through lumen 2. The wings are outwardly deflectable from the anchor body to form an angle therefrom of 10 to 60°, most preferably between 25 and 45°.

Figure 8A:
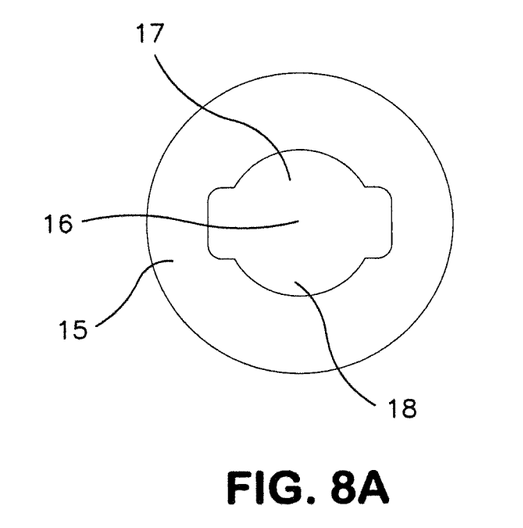
FIGS. 8A and 8B provide top and side views of the anchor screw head.
Figure 8B:
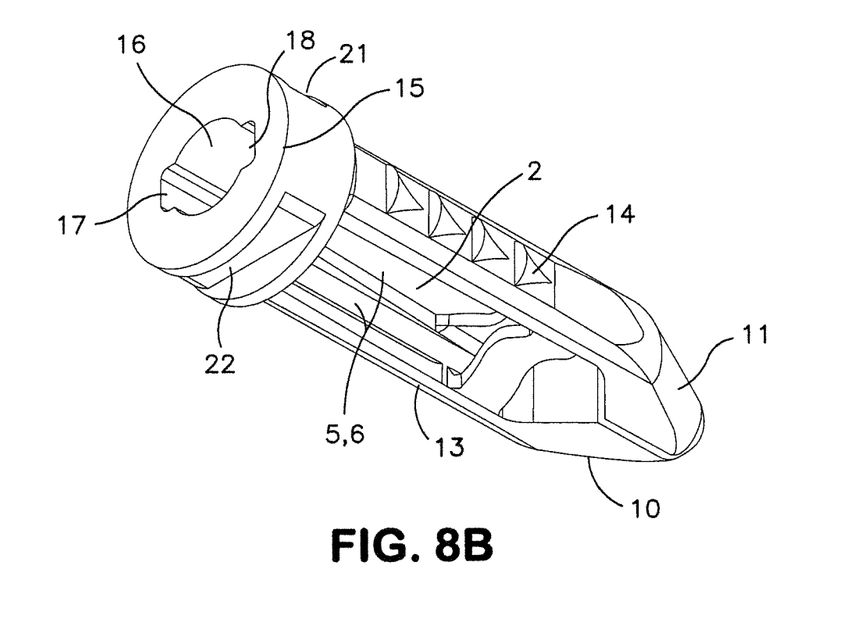
Figure 9:
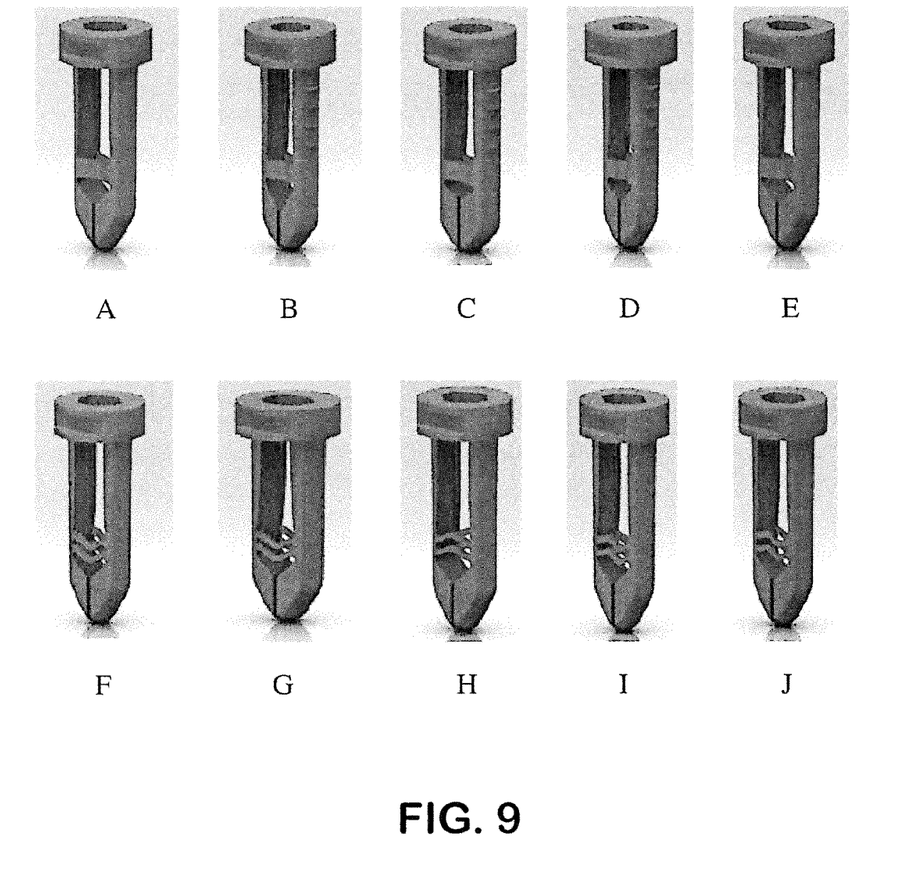
FIGS. 9A through 9J provide a side view of various embodiments of the invention.

To allow for universal application of the anchor, a screw head or nut 15 is provided per FIGS. 8A and 8B to facilitate insertion of the anchor into bone using any suitable installation tool (e.g., a surgical screwdriver). Anchor head 15 is made of a deformable material, such as a polymer with elastic properties such as rubber, or any of the materials described with regard to the composition of body 1.

Head 15 has a oval-shaped bore 16 therethrough that includes opposing slits 17 and 18 at the opposing ends of the oval, which allows bore 16 to stretch in diameter and shape to accommodate different sizes and shapes of installation devices and bone screws.

To minimize the volume occupied by the anchor assembly (including the screw) after installation, anchor head 15 may be a removable nut; i.e., one that is reversibly threaded onto the proximal end of the anchor and can be removed after the anchor and screw are fully introduced into the bone.

On insertion and rotation of a screw body through lumen 2, the rotation can exert a rotation force on body 1. Engagement of wings 10, 11 and flanges 13, 14 with surrounding bone will stabilize the anchor position. To further stabilize the anchor assembly during its implantation, anchor head 15 may be further provided with a pair of opposing recesses 21 and 22, as shown in FIG. 8B. Recesses 21, 22 provide a structure for engagement of a retaining tool, such as a hemostat, to hold the anchor assembly in place as it is being deployed.

Following insertion of a bone screw into the anchor body, the helical turns of the screw face will engage surrounding bone, stabilizing the anchor and screw in place within the bone. The inner diameter of lumen 2 is therefore adapted to allow for insertion of a screw through lumen 2 whereby the helical turns of the screw face will protrude from vertical slots 5, 6 to engage with surrounding bone.

It will be appreciated that the outer surfaces along body 1, wings 10, 11 and flanges 13, 14 can be treated to be especially well suited to a particular application (e.g., fixation or stabilization of bone at various levels of the spine). For example, the surfaces may be smooth, sanded, or micro-abrasive blasted to create a rough surface finish. A rough surface finish has the advantage of significantly increasing the friction coefficient between the device-bone interface. Additionally, said porous surfaces can promote bone growth and further strength the device-bone interface.

The anchor assembly may also be coated with a material, drug, or biologic to increase bone growth. For example, the device may be coated with hydroxyapatite, small molecules, or stem cells.

The invention having been fully described, its construction and use is illustrated by the examples below. The scope of the invention, however, is not limited by the examples but is defined instead by the appended claims.

EXAMPLES

Example 1

Construction of an Anchor Assembly According to the Invention

The device must be constrained to the dimensions of the anatomy of human vertebrae in order to attain a beneficial interaction. Thus, dimensions of an anchor assembly in accordance with the invention adapted for use in an average human L3 (lumbar level 3) vertebrae are provided in Figures illustrating each element of the anchor assembly. It will be appreciated that the dimensions illustrated are representative, and may be altered to accommodate variance in patient size, variance in level of the vertebra, and variance in pedicle screw size.

Example 2

Method for Use In L3 Vertebra

1. Surgeon inserts a 4 mm gear shift (pedicle probe) into pedicle and vertebral body to create a pilot hole. During this step, the surgeon assesses the quality of the patient's bone.
2. Surgeon determines that the quality of the patient's bone is poor.
3. Surgeon decides to augment the pedicle screw fixation by application of the device to reconstruct the strength of the pedicle.
4. Surgeon expands the pilot hole with a 6 mm gear shift.
5. Surgeon inserts the device into the 6 mm pilot hole.
6. Surgeon locks the device in proper orientation by attaching tool or tapping with mallet.
7. Surgeon inserts a pedicle screw into the device, causing the wings and, if present, flanges of the device to displace outward and improve the fixation strength of the pedicle screw.

What is claimed is:

1. A bone screw anchor assembly comprising:
   (a) an anchor body having proximal and distal ends joined by opposing walls flanked by adjacent vertical slots, said walls tapering at their distal ends to form opposing wings;
   (b) a lumen disposed through the anchor body and defined by said opposing walls, the inner diameter of the lumen allowing for insertion therethrough of a bone screw having helical turns which, on insertion, protrude through the vertical slots of the anchor body; and
   (c) a deformable collar joining the opposing walls of the anchor body proximal of the wings, which collar outwardly deforms on internal compression from an unexpanded to an expanded configuration, whereby the collar protrudes through the adjacent vertical slots when in the expanded configuration to engage surrounding bone and reinforce the anchor body;
   wherein the wings are outwardly deflectable on application of compressive force thereto exerted by insertion of a bone screw through the anchor body lumen, wherein such deflected wings engage surrounding bone to secure the anchor therein.

2. The assembly according to claim 1, wherein the wings are symmetrical in length.

3. The assembly according to claim 1, wherein the wings are asymmetrical in length.

4. The assembly according to claim 1, wherein the opposing walls of the anchor body are curved.

5. The assembly according to claim 1, wherein the vertical slots of the anchor body comprise between 50% and 75% of the diameter of the anchor body.

6. The assembly according to claim 1, wherein the anchor body is composed of a deformable biocompatible polymer or metal material.

7. The assembly according to claim 6, wherein each wing is outwardly deflectable from the anchor body to form an angle of 10 to 60° between each wing and a longitudinal axis of the anchor body.

8. The assembly according to claim 6, wherein the anchor body is composed of a biocompatible polymer selected from the group consisting of nylon, polyetheretherketone (PEEK), high density polyethylene, ultra-high molecular weight or high modulus polyethylene, polyethylene glycol, polyvinyl chloride (PVC), polymethyl methacrylate (PMMA) and polyvinyl alcohol (PVA).

9. The assembly according to claim 6, wherein the anchor body is composed of a biocompatible metal selected from the group consisting of titanium, nitinol and stainless steel.

10. The assembly according to claim 1, wherein each wing is connected to a wall of the anchor body by means of a hinge.

11. The assembly according to claim 1, further comprising a cylindrical anchor screw head attached to the proximal end of the anchor body, said head being adapted for engagement with an installation tool, wherein said adaption is provided by use of deformable materials to form the head and a bore through said head that is stretchable on insertion of an installation tool therein.

12. The assembly according to claim 11, wherein the head is further provided with opposing recesses in the sides, which recesses are sized to allow engagement of a retaining tool therewith to prevent rotation of the head during rotatable insertion of a bone screw through the head bore.

13. The assembly according to claim 1, wherein the collar is composed of a biocompatible polymer selected from the group consisting of nylon, polyetheretherketone (PEEK), high density polyethylene, ultra-high molecular weight or high modulus polyethylene, polyethylene glycol, polyvinyl chloride (PVC), polymethyl methacrylate (PMMA) and polyvinyl alcohol (PVA).

14. The assembly according to claim 1, wherein the collar is composed of is composed of a biocompatible metal selected from the group consisting of titanium, nitinol and stainless steel.

15. The assembly according to claim 1, wherein the collar in its unexpanded shape has opposing concave walls.

16. A bone screw anchor assembly comprising:
 (a) an anchor body having proximal and distal ends joined by opposing walls flanked by adjacent vertical slots, said walls tapering at their distal ends to form opposing wings;
 (b) a lumen disposed through the anchor body and defined by said opposing walls, the inner diameter of the lumen allowing for insertion therethrough of a bone screw;
 (c) at least one pair of opposing flanges disposed along the anchor body walls, wherein said flanges are outwardly deflectable in response to compressive force exerted on insertion therethrough of a bone screw; and,
 (d) a deformable collar disposed joining the opposing walls of the anchor body proximal of the wings, which collar outwardly deforms on internal compression from an unexpanded to an expanded configuration, whereby the collar protrudes through the adjacent vertical slots when in the circular configuration to engage surrounding bone and reinforce the anchor body;
 wherein the wings are outwardly deflectable on application of compressive force thereto exerted by insertion of a bone screw through the anchor body lumen, wherein such deflected wings engage surrounding bone to secure the anchor therein.

17. The assembly according to claim 16, wherein the inner diameter of the lumen is sized to allow for insertion therethrough of a bone screw having helical turns which, on insertion, protrude through the vertical slots of the anchor body.

18. The assembly according to claim 16, wherein each flange is connected to a wall of the anchor body by means of a hinge.

19. The assembly according to claim 16, wherein each flange is outwardly deflectable from the anchor body to form an angle of 10 to 60° between each flange and a longitudinal axis of the anchor body.

* * * * *